US009259723B2

(12) United States Patent
Aikawa et al.

(10) Patent No.: US 9,259,723 B2
(45) Date of Patent: Feb. 16, 2016

(54) QUATERNARY AMMONIUM SALT

(75) Inventors: Toshiaki Aikawa, Osaka (JP); Tetsuya Ikemoto, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 76 days.

(21) Appl. No.: 13/979,042

(22) PCT Filed: Jan. 30, 2012

(86) PCT No.: PCT/JP2012/052572
§ 371 (c)(1),
(2), (4) Date: Jul. 10, 2013

(87) PCT Pub. No.: WO2012/108367
PCT Pub. Date: Aug. 16, 2012

(65) Prior Publication Data

US 2013/0296552 A1 Nov. 7, 2013

(30) Foreign Application Priority Data

Feb. 8, 2011 (JP) ................................ 2011-024654

(51) Int. Cl.

| | |
|---|---|
| ***A61K 31/55*** | (2006.01) |
| ***C07D 223/14*** | (2006.01) |
| ***B01J 31/02*** | (2006.01) |
| ***C07B 53/00*** | (2006.01) |
| ***C07C 249/02*** | (2006.01) |
| ***C07D 223/18*** | (2006.01) |

(52) U.S. Cl.
CPC ............. *B01J 31/0285* (2013.01); *C07B 53/00* (2013.01); *C07C 249/02* (2013.01); *C07D 223/18* (2013.01)

(58) Field of Classification Search
CPC .............................. A61K 31/55; C07D 223/14
USPC ...................... 514/217; 540/587; 560/48, 124
See application file for complete search history.

(56) References Cited

U.S. PATENT DOCUMENTS

| | | | |
|---|---|---|---|
| 8,742,162 B2 * | 6/2014 | Aikawa et al. ................ | 560/124 |
| 2007/0135654 A1 | 6/2007 | Maruoka | |
| 2008/0107625 A1 | 5/2008 | D'Andrea et al. | |
| 2012/0130116 A1 | 5/2012 | Aikawa et al. | |

FOREIGN PATENT DOCUMENTS

| | | |
|---|---|---|
| JP | 2010-508361 A | 3/2010 |
| WO | WO 2005/073196 A1 | 8/2005 |
| WO | WO 2011/019066 A1 | 2/2011 |

OTHER PUBLICATIONS

Elsner et al., "Organocatalytic Asymmetric Conjugate Addition to Allenic Esters and Ketones", J. Am. Chem. Soc. 2008, vol. 130, pp. 4897-4905, XP2724682A.

Extended European Search Report, dated Jun. 10, 2014, for European Application No. 12745313.2.

International Preliminary Report on Patentability, issued on Aug. 13, 2013, for International Application No. PCT/JP2012/052572.

Written Opinion of the International Searching Authority, mailed on Mar. 13, 2012, for International Application No. PCT/JP2012/052572.

Beaulieu, P.L. et al., "Synthesis of (1R,2S)-1-Amino-2-vinylcyclopropanecarboxylic Acid (Vinyl-ACCA) Derivatives: Key Intermediates for the Preparation of Inhibitors of the Hepatitis C Virus NS3 Protease," J. Org. Chem., vol. 70, No. 15, 2005, pp. 5869-5879.

Belyk, K.M. et al., "Enantioselective Synthesis of (1R,2S)-1-Amino-2-vinylcyclopropanecarboxylic Acid Ethyl Ester (Vinyl-ACCA-OEt) by Asymmetric Phase-Transfer Catalyzed Cyclopropanation of (E)-N-Phenylmethyleneglycine Ethyl Ester," Organic Process Research & Development, vol. 14, No. 3, 2010, pp. 692-700.

Farina, V. et al., "The chemistry of Ru cyclopropylmethylidene complexes: Mechanistic studies and synthetic implications for the ring-closing metathesis reaction," Catalysis Today, vol. 140, 2009, pp. 74-83.

(Continued)

*Primary Examiner* — Brenda Coleman
(74) *Attorney, Agent, or Firm* — Birch, Stewart, Kolasch & Birch, LLP

(57) ABSTRACT

A quaternary ammonium salt represented by formula (5)

(5)

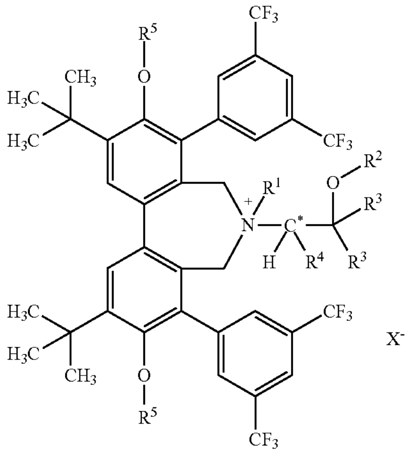

(wherein $R^1$ represents an alkyl group having 1 to 4 carbon atoms, $R^2$ represents an alkyl group having 1 to 10 carbon atoms, $R^3$ represents an alkyl group having 1 to 10 carbon atoms that is optionally substituted with one or more phenyl groups; or a phenyl group that optionally has one or more groups selected from the group consisting of alkyl groups having 1 to 10 carbon atoms and a trifluoromethyl group, $R^4$ represents an alkyl group having 1 to 4 carbon atoms, $R^5$ represents an alkyl group having 1 to 10 carbon atoms, C* represents an asymmetric carbon atom, and $X^-$ represents a halide ion) can be used as a catalyst having good stability under basic conditions.

13 Claims, No Drawings

(56) References Cited

OTHER PUBLICATIONS

International search report issued in PCT/JP2012/052572 mailed Mar. 13, 2012.

Lygo, B. et al., "Identification of a highly effective asymmetric phase-transfer catalyst derived from alpha-methylnaphthylamine," Tetrahedron Letters, vol. 44, 2003, pp. 5629-5632.

Lygo, B. et al., "Synthesis and Evaluation of Chiral Dibenzazepinium Halide Phase-Transfer Catalysts," Synlett, No. 4, 2009, pp. 675-680.

Melville, J.L. et al., "Exploring Phase-Transfer Catalysis with Molecular Dynamics and 3D/4D Quantitative Structure-Selectivity Relationships," J. Chem. Inf. Model, vol. 45, No. 4, 2005, pp. 971-981.

* cited by examiner

QUATERNARY AMMONIUM SALT

TECHNICAL FIELD

The present invention relates to a quaternary ammonium salt and a method for producing a cyclopropane compound using the same, and particularly relates to an optically active quaternary ammonium salt useful as an asymmetric catalyst and a method for producing an optically active cyclopropane compound using the optically active quaternary ammonium salt as an asymmetric catalyst.

BACKGROUND ART

It has been known that a cyclopropane compound such as (1R,2S)-1-(N-phenylmethylene)amino-2-vinylcyclopropanecarboxylic acid ester is useful as a production intermediate of pharmaceuticals such as an anti-hepatitis C agent [for example, see Organic Process Research & Development, vol. 14, pages 692 to 700, (2010)].

Concerning a method for producing a cyclopropane compound, a method of reacting N-phenylmethylene glycine ester with (E)-1,4-dibromo-2-butene in the presence of a N-benzylcinchonidinium compound and sodium hydroxide to obtain (1R,2S)-1-(N-phenylmethylene)amino-2-vinylcyclopropanecarboxylic acid ester is known in the above document. In the above-described method, 0.03 mol of a N-benzylcinchonidinium compound is used as an asymmetric catalyst, based on 1 mol of N-phenylmethylene glycine ester, and further, the reaction is carried out in the presence of sodium hydroxide.

The N-benzylcinchonidinium compound used as an asymmetric catalyst in the above method is not always satisfactory in stability under basic conditions. Therefore, when the N-benzylcinchonidinium compound is used in the reaction in the presence of sodium hydroxide, the N-benzylcinchonidinium compound sometimes decomposes during the reaction. In this case, there was a problem that a large amount of N-benzylcinchonidinium compound has to be used.

Therefore, the development of a new catalyst excellent in stability under basic conditions has been required.

SUMMARY OF THE INVENTION

The present invention provides a quaternary ammonium salt represented by formula (5) available as a catalyst excellent in stability under basic conditions.

More specifically, the present invention is as described below.

[1] A quaternary ammonium salt represented by formula (5)

(5)

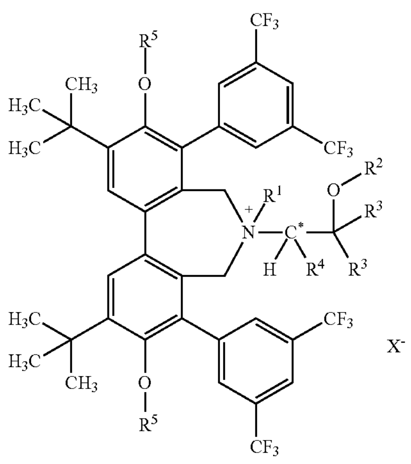

(wherein $R^1$ represents an alkyl group having 1 to 4 carbon atoms, $R^2$ represents an alkyl group having 1 to 10 carbon atoms, $R^3$ represents an alkyl group having 1 to 10 carbon atoms that is optionally substituted with one or more phenyl groups; or a phenyl group that optionally has one or more groups selected from the group consisting of alkyl groups having 1 to 10 carbon atoms and a trifluoromethyl group, $R^4$ represents an alkyl group having 1 to 4 carbon atoms, $R^5$ represents an alkyl group having 1 to 10 carbon atoms, C* represents an asymmetric carbon atom, and $X^-$ represents a halide ion).

[2] The quaternary ammonium salt according to [1], wherein the quaternary ammonium salt represented by formula (5) is an optically active compound based on the asymmetric carbon atom of C*.

[3] The quaternary ammonium salt according to [1] or [2], wherein both $R^1$ and $R^4$ in formula (5) are a methyl group.

[4] The quaternary ammonium salt according to any one of [1] to [3], wherein both $R^2$ and $R^5$ in formula (5) are a methyl group.

[5] The quaternary ammonium salt according to any one of [1] to [4], wherein $R^3$ in formula (5) is an ethyl group, a butyl group, a hexyl group, an octyl group, a 2-phenylethyl group, or a p-tolyl group.

[6] A method for producing a cyclopropane compound represented by formula (3)

(3)

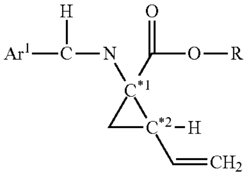

(wherein $Ar^1$ represents an optionally substituted phenyl group or an optionally substituted naphthyl group, and R represents an alkyl group having 1 to 12 carbon atoms or an alkenyl group having 2 to 12 carbon atoms, $C^{*1}$ and $C^{*2}$ represent an asymmetric carbon atom, $C^{*2}$ is an S-configuration when $C^{*1}$ is an R-configuration, and $C^{*2}$ is an R-configuration when $C^{*1}$ is an S-configuration), comprising a step of reacting a compound represented by formula (1)

(1)

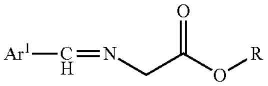

(wherein $Ar^1$ and R are as defined above) with a compound represented by formula (2)

(2)

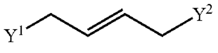

(wherein $Y^1$ and $Y^2$ each independently represent a halogen atom, an alkanesulfonyloxy group having 1 to 6 carbon atoms, a perfluoroalkanesulfonyloxy group having 1 to 6 carbon atoms, or a benzenesulfonyloxy group. Herein, a hydrogen atom or atoms contained in the benzenesulfonyloxy group may be each independently substituted with one or more groups selected from the group consisting of alkyl groups having 1 to 6 carbon atoms, halogen atoms, and a nitro group), in the presence of a quaternary ammonium salt represented by formula (5)

(5)

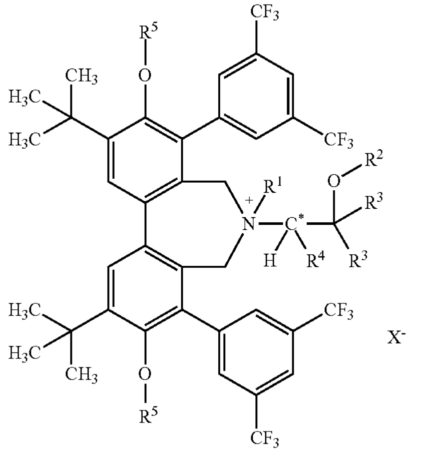

(wherein $R^1$ represents an alkyl group having to 4 carbon atoms, $R^2$ represents an alkyl group having 1 to 10 carbon atoms, $R^3$ represents an alkyl group having 1 to 10 carbon atoms that is optionally substituted with one or more phenyl groups; or a phenyl group that optionally has one or more groups selected from the group consisting of alkyl groups having 1 to 10 carbon atoms and a trifluoromethyl group, $R^4$ represents an alkyl group having 1 to 4 carbon atoms, $R^5$ represents an alkyl group having 1 to 10 carbon atoms, C* represents an asymmetric carbon atom, and $X^-$ represents a halide ion) and a base.

[7] The method for producing a cyclopropane compound according to [6], wherein the quaternary ammonium salt represented by formula (5) and the cyclopropane compound represented by formula (3) are both optically active.

Mode for Carrying Out the Invention $R^1$ in formula (5) represents an alkyl group having 1 to 4 carbon atoms. Examples of the alkyl group having 1 to 4 carbon atoms include straight-chain alkyl groups having 1 to 4 carbon atoms, and specific examples are a methyl group, an ethyl group, a propyl group, and a butyl group. $R^1$ is preferably a methyl group.

$R^2$ in formula (5) represents an alkyl group having 1 to 10 carbon atoms. Examples of the alkyl group having 1 to 10 carbon atoms include straight-chain or branched alkyl groups having 1 to 10 carbon atoms, and specific examples are a methyl group, an ethyl group, a propyl group, a butyl group, an isobutyl group, a pentyl group, an isopentyl group, a neopentyl group, a hexyl group, an isohexyl group, a heptyl group, an isoheptyl group, an octyl group, a nonyl group, and a decyl group. $R^2$ is preferably a methyl group, an ethyl group, a propyl group, a butyl group, or an isobutyl group, and more preferably a methyl group.

$R^3$ in formula (5) represents an alkyl group having 1 to 10 carbon atoms that is optionally substituted with one or more phenyl groups; or a phenyl group that optionally has one or more groups selected from the group consisting of alkyl groups having 1 to 10 carbon atoms and a trifluoromethyl group.

Examples of the alkyl group having 1 to 10 carbon atoms that is optionally substituted with one or more phenyl groups include a methyl group, an ethyl group, a propyl group, an isopropyl group, a butyl group, a 2-butyl group, an isobutyl group, a t-butyl group, a pentyl group, a hexyl group, a heptyl group, an octyl group, a nonyl group, a decyl group, a benzyl group, and a 2-phenylethyl group.

Examples of the phenyl group that optionally has a group selected from the group consisting of alkyl groups having 1 to 10 carbon atoms and a trifluoromethyl group include a phenyl group, an o-tolyl group, a m-tolyl group, a p-tolyl group, a 2,3-dimethylphenyl group, a 2,4-dimethylphenyl group, a 2,5-dimethylphenyl group, a 2,6-dimethylphenyl group, a 3,4-dimethylphenyl group, a 3,5-dimethylphenyl group, a 2-ethylphenyl group, a 3-ethylphenyl group, a 4-ethylphenyl group, a 2-trifluoromethylphenyl group, a 4-trifluoromethylphenyl group, a 3,5-bis(trifluoromethyl)phenyl group, and a 2-methyl-3-trifluoromethylphenyl group.

$R^3$ is preferably an alkyl group having 2 to 8 carbon atoms that is optionally substituted with one or more phenyl groups, or a phenyl group that is optionally substituted with one or more alkyl groups having 1 to 10 carbon atoms, more preferably a 2-phenylethyl group, a butyl group, a pentyl group, a hexyl group, a heptyl group or an octyl group, and further preferably a 2-phenylethyl group.

$R^4$ in formula (5) represents an alkyl group having 1 to 4 carbon atoms. Examples of the alkyl group having 1 to 4 carbon atoms include straight-chain alkyl groups having 1 to 4 carbon atoms, and specific examples are a methyl group, an ethyl group, a propyl group, and a butyl group. $R^4$ is preferably a methyl group.

$R^5$ in formula (5) represents an alkyl group having 1 to 10 carbon atoms. Examples of the alkyl group having 1 to 10 carbon atoms include straight-chain or branched alkyl groups having 1 to 10 carbon atoms, and specific examples are a methyl group, an ethyl group, a propyl group, a butyl group, an isobutyl group, a pentyl group, an isopentyl group, a neopentyl group, a hexyl group, an isohexyl group, a heptyl group, an isoheptyl group, an octyl group, a nonyl group, and a decyl group. $R^5$ is preferably a methyl group, an ethyl group, a propyl group, a butyl group or an isobutyl group, and more preferably a methyl group.

$X^-$ in formula (5) represents a halide ion. Examples of the halide ion include a chloride ion, a bromide ion, and an iodide ion. $X^-$ is preferably a chloride ion or a bromide ion and more preferably a bromide ion.

Examples of the quaternary ammonium salt represented by formula (5) (compound (5)) specifically include quaternary ammonium salts represented by the following formulae (5-1) to (5-12), and enantiomers thereof.

(5-1)

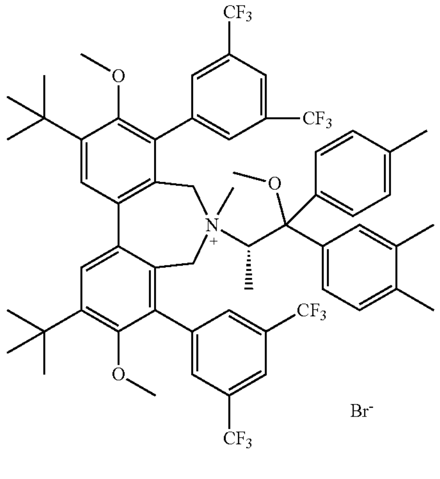

-continued
(5-2)
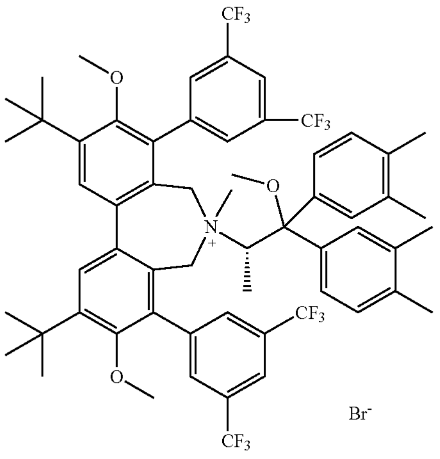
(5-3)
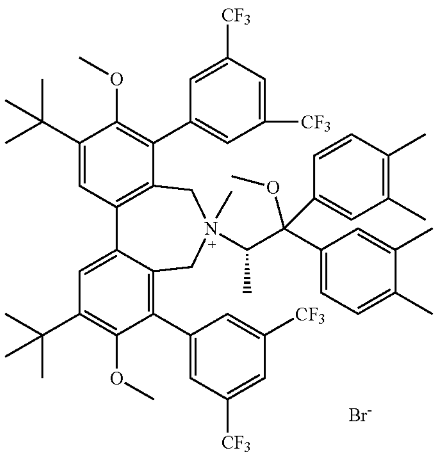
(5-4)
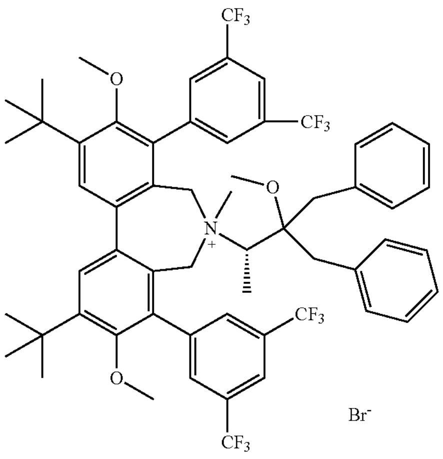
-continued
(5-5)
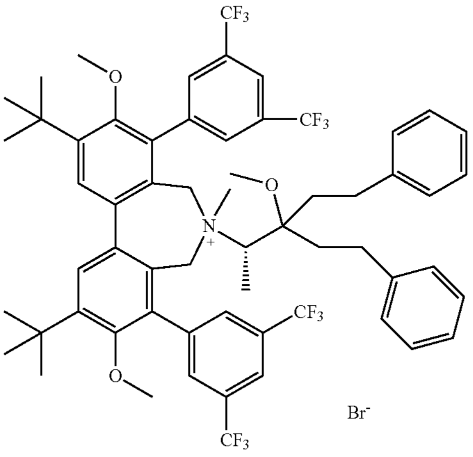
(5-6)
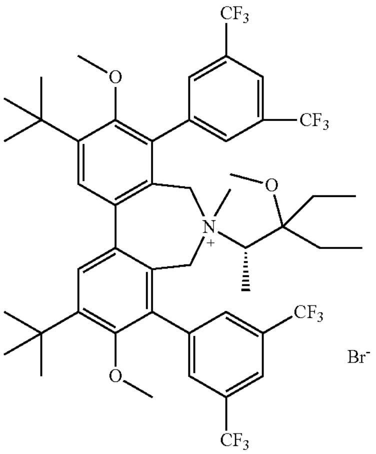
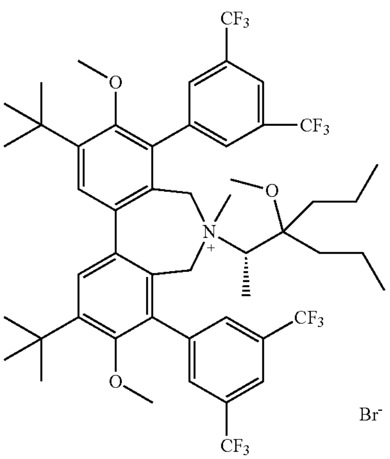

-continued (5-8)

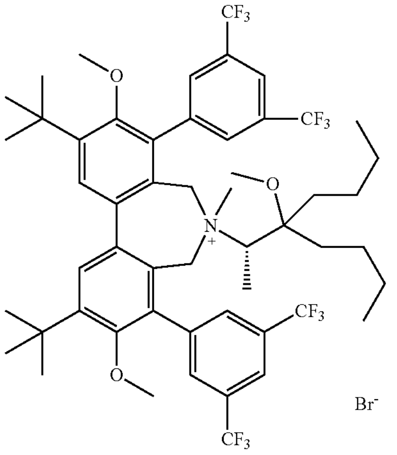

(5-9)

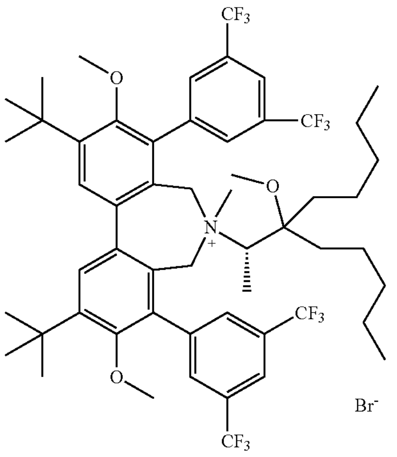

(5-10)

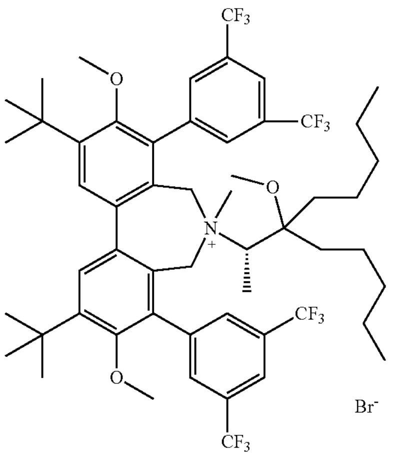

-continued (5-11)

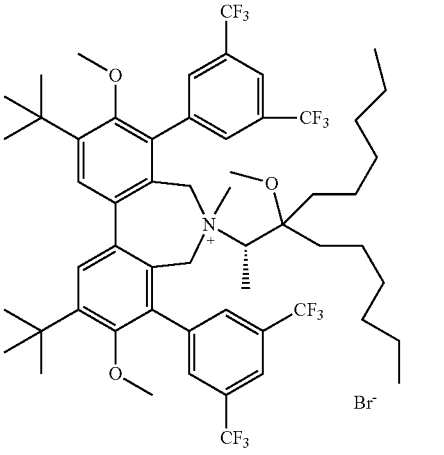

(5-12)

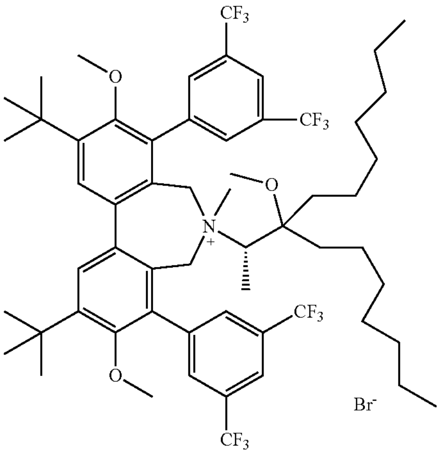

The compound (5) is preferably a quaternary ammonium salt represented by formula (5-1), a quaternary ammonium salt represented by formula (5-5), a quaternary ammonium salt represented by formula (5-6), a quaternary ammonium salt represented by formula (5-7), a quaternary ammonium salt represented by formula (5-8), a quaternary ammonium salt represented by formula (5-9), a quaternary ammonium salt represented by formula (5-10), a quaternary ammonium salt represented by formula (5-11), a salt represented by formula (5-12) or an enantiomer thereof, more preferably a quaternary ammonium salt represented by formula (5-5), a quaternary ammonium salt represented by formula (5-8), a quaternary ammonium salt represented by formula (5-9), a quaternary ammonium salt represented by formula (5-10), a quaternary ammonium salt represented by formula (5-11), a salt represented by formula (5-12) or an enantiomer thereof, and further preferably a quaternary ammonium salt represented by formula (5-5) or an enantiomer thereof.

The compound (5) is produced by a reaction of a compound represented by formula (6) (compound (6))

(6)

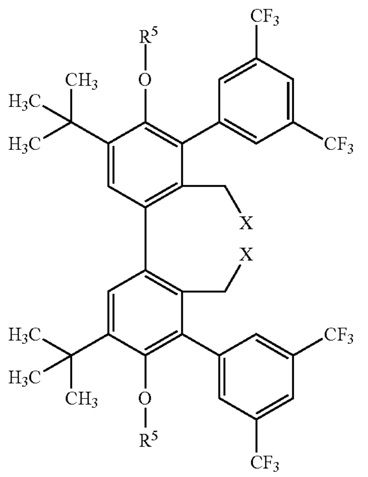

(wherein $R^5$ is as defined above, and X represents a halogen atom) with a compound represented by formula (7) (compound (7))

(7)

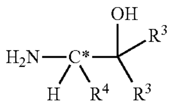

(wherein $R^3$, $R^4$ and C* are as defined above)
(ammonium salt forming reaction).

X in formula (6) represents a halogen atom (for example, a chlorine atom, a bromine atom, and an iodine atom), and X is preferably a chlorine atom or a bromine atom and more preferably a bromine atom.

The compound (6) is produced, for example, by the method described in Tetrahedron Letters, vol. 44, pages 5629 to 5632 (2003).

The compound (7) is produced, for example, by the method shown below.

First, a compound represented by formula (7-1) (compound (7-1-1))

$R^3$—Mg—Br (7-1-1)

(wherein $R^3$ is as defined above)
is allowed to react with a compound represented by formula (7-1-2) (compound (7-1-2))

(7-1-2)

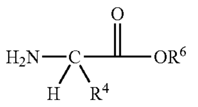

(wherein $R^4$ is as defined above, and $R^6$ represents, for example, a hydrocarbon group such as a methyl group, an ethyl group, or a benzyl group)
or an acid addition salt thereof in the presence or absence of a tertiary amine such as triethylamine, and then, an amino group (—$NH_2$) contained in the obtained compound represented by formula (7-2) (compound (7-2))

(7-2)

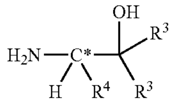

(wherein $R^3$, $R^4$ and C* are as defined above)
is protected. Then, the obtained compound represented by formula (7-3) (compound (7-3)), (7-3)

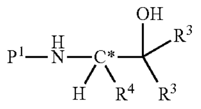

(wherein $R^3$, $R^4$ and C* are as defined above, and $P^1$ represents, for example, a protective group such as a benzyl group, a 2,4-dimethoxybenzyl group, a tert-butoxycarbonyl group, or a benzyloxycarbonyl group)
Is allowed to react with a base such as sodium hydride, and an alkylating agent, and the protected amino group contained in the obtained compound represented by formula (7-4) (compound (7-4))

(7-4)

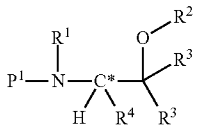

(wherein $R^1$, $R^2$, $R^3$, $R^4$, $P^1$ and C* are as defined above) is deprotected, whereby the compound (7) can be obtained.

Here, the alkylating agent is an alkylating agent that can introduce an alkyl group having 1 to 4 carbon atoms represented by $R^1$ and an alkyl group having 1 to 10 carbon atoms represented by $R^2$ into the compound (7-3), and specific examples include iodomethane, iodoethane, 1-iodobutane, and dimethyl sulfate.

The ammonium salt forming reaction is preferably carried out in the presence of a base. Examples of the base include alkali metal hydroxides such as sodium hydroxide, potassium hydroxide and cesium hydroxide, alkali metal carbonates such as potassium carbonate and sodium carbonate, alkali metal bicarbonates such as sodium bicarbonate and potassium bicarbonate, and tertiary amines such as triethylamine and diisopropylethylamine.

The base is preferably an alkali metal carbonate compound or an alkali metal bicarbonate compound, and more preferably sodium bicarbonate.

The ammonium salt forming reaction is preferably carried out in a solvent. Examples of the solvent include aliphatic hydrocarbon solvents, aromatic solvents, ether solvents, alcohol solvents, nitrile solvents, ketone solvents, chlorinated aliphatic hydrocarbon solvents, and aprotic polar solvents. These solvents may be used singly or in a mixture of two or more kinds thereof.

Examples of the aliphatic hydrocarbon solvent include pentane, hexane, isohexane, heptane, isoheptane, octane, isooctane, nonane, isononane, decane, isodecane, undecane, dodecane, cyclopentane, cyclohexane, methylcyclohexane, t-butylcyclohexane, and petroleum ether.

Examples of the aromatic solvent include benzene, toluene, ethylbenzene, isopropylbenzene, t-butylbenzene, xylene, mesitylene, monochlorobenzene, monofluorobenzene, α,α,α-trifluoromethylbenzene, 1,2-dichlorobenzene, 1,3-dichlorobenzene, 1,2,3-trichlorobenzene, and 1,2,4-trichlorobenzene.

Examples of the ether solvent include tetrahydrofuran, methyltetrahydrofuran, diethyl ether, dipropyl ether, diisopropyl ether, dibutyl ether, dipentyl ether, dihexyl ether, diheptyl ether, dioctyl ether, t-butyl methyl ether, cyclopentyl methyl ether, 1,2-dimethoxyethane, diethyleneglycoldimethyl ether, anisol, and diphenyl ether.

Examples of the alcohol solvent include methanol, ethanol, 1-propanol, 2-propanol, butyl alcohol, isobutyl alcohol, t-butyl alcohol, 1-pentanol, 2-pentanol, isopentyl alcohol, 1-hexanol, 2-hexanol, isohexyl alcohol, 1-heptanol, 2-heptanol, 3-heptanol, isoheptyl alcohol, ethylene glycol monomethyl ether, ethylene glycol monoethyl ether, ethylene glycol monopropyl ether, ethylene glycol monoisopropyl ether, ethylene glycol monobutyl ether, ethylene glycol monoisobutyl ether, ethylene glycol mono t-butyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether, and diethylene glycol mono t-butyl ether.

Examples of the nitrile solvent include acetonitrile, propionitrile, and benzonitrile.

Examples of the ketone solvent include acetone, methyl ethyl ketone, and methyl isobutyl ketone.

Examples of the chlorinated aliphatic hydrocarbon solvent include dichloromethane, chloroform, and 1,2-dichloroethane.

Examples of the aprotic polar solvent include dimethyl sulfoxide, sulfolane, N,N-dimethylformamide, N,N-dimethylacetamide, N,N-dimethylpropionamide, N-methylpyrrolidone, γ-butyrolactone, dimethyl carbonate, diethyl carbonate, ethylene carbonate, propylene carbonate, 1,3-dimethyl-2-imidazolidinone, and 1,3-dimethyl-3,4,5,6-tetrahydro-2(1H)-pyridinone.

The solvent in the ammonium salt forming reaction is preferably a nitrile solvent or a ketone solvent, and more preferably a ketone solvent.

The ammonium salt forming reaction is performed, for example, by the following method.

(i) A method of reacting compound (6) with compound (7) by adding compound (6) and a base to a mixture of compound (7) and a solvent and adjusting the temperature of the obtained mixture to the reaction temperature described below.

(ii) A method of reacting compound (6) with compound (7) by adding compound (7) and a base to a mixture of compound (6) and a solvent and adjusting the temperature of the obtained mixture to the reaction temperature described below.

(iii) A method of reacting compound (6) with compound (7) by adjusting the temperature of a mixture of compound (7) and a solvent to the reaction temperature described below and adding compound (6) and a base thereto.

(iv) A method of reacting compound (6) with compound (7) by adjusting the temperature of a mixture of compound (6) and a solvent to the reaction temperature described below and adding compound (7) and a base thereto.

(v) A method of reacting compound (6) with compound (7) by adjusting the temperature of a solvent and a base to the reaction temperature described below and adding compound (6) and compound (7) thereto.

The amount of the compound (7) used in the ammonium salt forming reaction is, for example, within a range from 0.8 to 4 mol, preferably within a range from 1 to 2 mol, and more preferably within a range from 1.0 to 1.5 mol, based on 1 mol of the compound (6). When the use amount of the compound (7) is less than 0.8 mol, the yield of compound (5) is likely to decrease.

The amount of the base used in the ammonium salt forming reaction is, for example, within a range from 0.5 to 2 mol, preferably within a range from 0.8 to 1.5 mol, and more preferably within a range from 1.0 to 1.3 mol, based on 1 mol of the compound (6). When the amount of the base is less than 0.8 mol, the yield of compound (5) is likely to decrease.

When the ammonium salt forming reaction is performed in the presence of a solvent, the amount of the solvent is, for example, within a range from 1 to 50 mL, and preferably within a range from 2 to 20 mL, based on 1 g of the compound (6).

The reaction temperature in the ammonium salt forming reaction is a temperature selected, for example, from a range from 40° C. to 100° C., and a temperature selected preferably from a range from 45° C. to 80° C. When the reaction temperature is less than 45° C., the rate of the ammonium salt forming reaction tends to reduce, and when the reaction temperature is above 100° C., the yield of compound (5) tends to decrease.

After completion of the ammonium salt forming reaction, the obtained compound (5) may be isolated and may not be isolated. The compound (5) can be isolated by subjecting the reaction mixture after completion of the ammonium salt forming reaction, for example, to a post-treatment such as neutralization, extraction washing and washing with water, as necessary, then subjecting, for example, to a crystallization treatment such as cooling crystallization and concentration crystallization, and collecting a precipitate. The isolated compound (5) is purified, for example, by recrystallization, whereby the chemical purity of compound (5) can be improved, and when the compound (5) is optically active, the chemical purity can also be improved. When the compound (5) is optically active, the chemical purity is not limited, and is, for example, 90% e.e. (hereinafter, e.e. represents enantiomer excess) or more, preferably 95% e.e. or more, and further preferably 98% e.e. or more.

The compound (5) obtained as described above can be used as a catalyst. When the compound (5) is optically active, the compound (5) can be used as an asymmetric catalyst. In addition, the compound (5) is excellent in stability under basic conditions, for example, compared to a N-benzylcinchonidinium compound and the like. Therefore, even when the compound (5) is used as a catalyst in the presence of a base, decomposition in the reaction is suppressed, and the amount can be reduced compared to the case of using a N-benzylcinchonidinium compound.

Hereinbelow, the method for producing an optically active cyclopropane compound using the compound (5) as a catalyst will be described in detail.

A cyclopropane compound represented by formula (3) (compound (3)) can be produced by reacting a compound represented by formula (1) (compound (1)) with a compound represented by formula (2) (compound (2)), in the presence of the compound (5) and a base. The above reaction may be referred to as the present catalytic reaction.

$Ar^1$ in formula (1) represents an optionally substituted phenyl group or an optionally substituted naphthyl group. Here, the naphthyl group may be either a 1-naphthyl group or a 2-naphthyl group. Examples of the substituent in which the phenyl group and naphthyl group may have include alkyl groups having 1 to 12 carbon atoms, alkoxy groups having 1 to 12 carbon atoms, halogen atoms (for example, fluorine atom, chlorine atom, and bromine atom), a nitro group, a cyano group, and a trifluoromethyl group.

Here, the alkyl groups having 1 to 12 carbon atoms include straight-chain or branched alkyl groups having 1 to 12 carbon atoms such as a methyl group, an ethyl group, a propyl group, an isopropyl group, a butyl group, an isobutyl group, a t-butyl group, a pentyl group, a hexyl group, a heptyl group, an octyl group, a nonyl group, a decyl group, an undecyl group and a dodecyl group, and cyclic alkyl groups having 3 to 12 carbon atoms such as a cyclopropyl group, a cyclobutyl group, a cyclopentyl group, a cyclohexyl group, a cycloheptyl group and a cyclooctyl group. The alkoxy groups having 1 to 12 carbon atoms include straight-chain or branched alkoxy groups having 1 to 12 carbon atoms such as a methoxy group, an ethoxy group, a propoxy group, an isopropoxy group, a butoxy group, an isobutoxy group, a t-butoxy group, a pentyloxy group, a hexyloxy group, a heptyloxy group and an octyloxy group, and cyclic alkoxy groups having 3 to 12 carbon atoms such as a cyclopropyloxy group, a cyclobutyloxy group, a cyclopentyloxy group, a cyclohexyloxy group, a cycloheptyloxy group and a cyclooctyloxy group.

Specific examples of $Ar^1$ include a phenyl group, a 1-naphthyl group, a 2-naphthyl group, a 2-methylphenyl group, a 2-methoxyphenyl group, a 2-fluorophenyl group, a 2-chlorophenyl group, a 2-bromophenyl group, a 2-nitrophenyl group, a 2-cyanophenyl group, a 2-(trifluoromethyl)phenyl group, a 3-methylphenyl group, a 3-methoxyphenyl group, a 3-fluorophenyl group, a 3-chlorophenyl group, a 3-bromophenyl group, a 3-nitrophenyl group, a 3-cyanophenyl group, a 3-(trifluoromethyl)phenyl group, a 4-methylphenyl group, a 4-methoxyphenyl group, a 4-fluorophenyl group, a 4-chlorophenyl group, a 4-bromophenyl group, a 4-nitrophenyl group, a 4-cyanophenyl group, a 4-(trifluoromethyl)phenyl group, a 2,3-dichlorophenyl group, a 2,4-dichlorophenyl group, a 3,4-dichlorophenyl group, and a 3,4,5-trichlorophenyl group.

$Ar^1$ is preferably an optionally substituted phenyl group, more preferably a phenyl group that may be substituted with a halogen atom, and further preferably a phenyl group or a 4-chlorophenyl group.

R in formula (1) represents an alkyl group having 1 to 12 carbon atoms or an alkenyl group having 2 to 12 carbon atoms. Examples of the alkyl group having 1 to 12 carbon atoms include straight-chain or branched alkyl groups having 1 to 12 carbon atoms such as a methyl group, an ethyl group, a propyl group, an isopropyl group, a butyl group, an isobutyl group, a t-butyl group, a pentyl group, a hexyl group, a heptyl group, an octyl group, a nonyl group, a decyl group, an undecyl group and a dodecyl group, and cyclic alkyl groups having 3 to 12 carbon atoms such as a cyclopropyl group, a cyclobutyl group, a cyclopentyl group, a cyclohexyl group, a cycloheptyl group and a cyclooctyl group. Examples of the alkenyl group having 2 to 12 carbon atoms represented by R include straight-chain or branched alkenyl group such as an ethenyl group, a 2-propenyl group, a 2-butenyl group and a 3-methyl-2-butenyl group, and cyclic alkenyl groups such as a 1-cyclohexenyl group.

R is preferably an alkyl group having 1 to 12 carbon atoms, more preferably an ethyl group or a t-butyl group, and further preferably an ethyl group.

Examples of the compound (1) include N-phenylmethyleneglycine ethyl ester, N-naphthalen-1-ylmethyleneglycine ethyl ester, N-naphthalen-2-ylmethyleneglycine ethyl ester, N-(4-methylphenyl)methyleneglycine ethyl ester, N-(4-methoxyphenyl)methyleneglycine ethyl ester, N-(4-fluorophenyl)methyleneglycine ethyl ester, N-(4-chlorophenyl)methyleneglycine ethyl ester, N-[4-(trifluoromethyl)phenyl]methyleneglycine ethyl ester, N-(3-chlorophenyl)methyleneglycine ethyl ester, N-(4-chlorophenyl)methyleneglycine ethyl ester, N-phenylmethyleneglycine t-butyl ester, N-(4-chlorophenyl)methyleneglycine t-butyl ester, N-phenylmethyleneglycine methyl ester, and N-(4-chlorophenyl)methyleneglycine methyl ester.

The compound (1) is preferably N-phenylmethyleneglycine ethyl ester, N-naphthalen-1-ylmethyleneglycine ethyl ester, or N-(4-chlorophenyl)methyleneglycine ethyl ester.

The compound (1) can be produced, for example, by the method described in Organic Process Research & Development, 2010, vol. 14, pages 692 to 700 and the like, using a glycine ester such as glycine ethyl ester hydrochloride as a raw material. In addition, commercially available products such as N-phenylmethyleneglycine ethyl ester can also be used.

$Y^1$ and $Y^2$ in formula (2) each independently represent a halogen atom, an alkanesulfonyloxy group having 1 to 6 carbon atoms, a perfluoroalkanesulfonyloxy group having 1 to 6 carbon atoms, or a benzenesulfonyloxy group. Examples of the halogen atom include a chlorine atom, a bromine atom and an iodine atom, Examples of the alkanesulfonyloxy group having 1 to 6 carbon atoms include a methanesulfonyloxy group, an ethanesulfonyloxy group, a propanesulfonyloxy group, a butanesulfonyloxy group, a pentanesulfonyloxy group and a hexanesulfonyloxy group, and examples of the perfluoroalkanesulfonyloxy group having 1 to 6 carbon atoms include a trifluoromethanesulfonyloxy group, a pentafluoroethanesulfonyloxy group, a perfluoropropanesulfonyloxy group and a perfluorohexanesulfonyloxy group.

Here, the hydrogen atoms in the benzenesulfonyloxy group may be each independently substituted with one or more groups selected from the group consisting of alkyl groups having 1 to 6 carbon atoms, halogen atoms and a nitro group. Examples of the alkyl group having 1 to 6 carbon atoms include a methyl group, an ethyl group, a propyl group, an isopropyl group, a butyl group, and t-butyl. Examples of the halogen atom include a fluorine atom, a chlorine atom, and a bromine atom. Examples of the benzenesulfonyloxy group having the above substituent include a 4-methylbenzenesulfonyloxy group, a 2-nitrobenzenesulfonyloxy group, a 3-nitrobenzenesulfonyloxy group, a 4-nitrobenzenesulfonyloxy group, a 2,4-dinitrobenzenesulfonyloxy group, a 4-fluorobenzenesulfonyloxy group, and a pentafluorobenzenesulfonyloxy group.

$Y^1$ and $Y^2$ each independently represent preferably a chlorine atom, a bromine atom or a methanesulfonyloxy group, and more preferably a bromine atom.

Examples of the compound (2) include (E)-1,4-dibromo-2-butene, (E)-1,4-dichloro-2-butene, (E)-1,4-dimethanesulfonyloxy-2-butene, and (E)-1-bromo-4-chloro-2-butene. The compound (2) is preferably (E)-1,4-dibromo-2-butene or (E)-1,4-dichloro-2-butene, and more preferably (E)-1,4-dibromo-2-butene.

The compound (2) can be produced by a known method, and commercially available products can also be used as they are.

$Ar^1$ and R in formula (3) are as defined as $Ar^1$ and R in formula (1).

The compound (3) is a compound which has an arylmethylideneamino group represented by $-N{=}CH-Ar^1$ and an ethenyl group represented by —CH═CH$_2$ on a mutually different surface side with respect to a cyclopropane ring plane.

In the compound (3), there exist, as the optical isomers, isomers having an arylmethylideneamino group and an ethenyl group on the same surface side with respect to a cyclopropane ring plane, which are each represented by formula (3c)

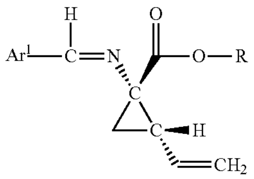

(3c)

(wherein Ar$^1$ and R are as defined above), and formula (3d)

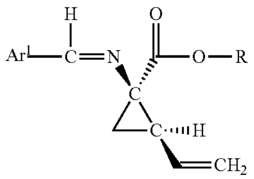

(3d)

(wherein Ar$^1$ and R are as defined above). Hereinafter, these isomers may be collectively referred to as diastereomer (3c-d).

Examples of the compound (3) include (1S,2R)-1-(N-phenylmethylene)amino-2-vinylcyclopropanecarboxylic acid ethyl ester, (1S,2R)-1-[N-(4-chlorophenyl)methylene]amino-2-vinylcyclopropanecarboxylic acid ethyl ester, (1S,2R)-1-(N-phenylmethylene)amino-2-vinylcyclopropanecarboxylic acid t-butyl ester, (1S,2R)-1-[N-(4-chlorophenyl)methylene]amino-2-vinylcyclopropanecarboxylic acid t-butyl ester, (1S,2R)-1-(N-phenylmethylene)amino-2-vinylcyclopropanecarboxylic acid methyl ester, (1S,2R)-1-[N-(4-chlorophenyl)methylene]amino-2-vinylcyclopropanecarboxylic acid methyl ester, (1S,2R)-1-(N-naphthalen-1-ylmethylene)amino-2-vinylcyclopropanecarboxylic acid ethyl ester, (1R,2S)-1-(N-phenylmethylene)amino-2-vinylcyclopropanecarboxylic acid ethyl ester, (1R,2S)-1-[N-(4-chlorophenyl)methylene]amino-2-vinylcyclopropanecarboxylic acid ethyl ester, (1R,2S)-1-(N-phenylmethylene)amino-2-vinylcyclopropanecarboxylic acid t-butyl ester, (1R,2S)-1-[N-(4-chlorophenyl)methylene]amino-2-vinylcyclopropanecarboxylic acid t-butyl ester, (1R,2S)-1-(N-phenylmethylene)amino-2-vinylcyclopropanecarboxylic acid methyl ester, (1R,2S)-1-[N-(4-chlorophenyl)methylene]amino-2-vinylcyclopropanecarboxylic acid methyl ester, and (1R,2S)-1-(N-naphthalen-1-ylmethylene)amino-2-vinylcyclopropanecarboxylic acid ethyl ester.

Examples of the base used in the present catalytic reaction include alkali metal hydroxides such as sodium hydroxide, potassium hydroxide and cesium hydroxide, alkali metal carbonate compounds such as potassium carbonate and sodium carbonate, and tertiary amines such as triethylamine and diisopropylethylamine. The base is preferably an alkali metal hydroxide and more preferably potassium hydroxide.

The present catalytic reaction is preferably performed in the presence of a solvent. Examples of the solvent include aliphatic hydrocarbon solvents, aromatic solvents, ether solvents, alcohol solvents, nitrile solvents, ester solvents, chlorinated aliphatic hydrocarbon solvents, aprotic polar solvents, and water. These solvents may be used singly or in a mixture of two or more kinds thereof.

Examples of the aliphatic hydrocarbon solvent include pentane, hexane, isohexane, heptane, isoheptane, octane, isooctane, nonane, isononane, decane, isodecane, undecane, dodecane, cyclopentane, cyclohexane, methylcyclohexane, t-butylcyclohexane, and petroleum ether. Examples of the aromatic solvent include benzene, toluene, ethylbenzene, isopropylbenzene, t-butylbenzene, xylene, mesitylene, monochlorobenzene, monofluorobenzene, α,α,α-trifluoromethylbenzene, 1,2-dichlorobenzene, 1,3-dichlorobenzene, 1,2,3-trichlorobenzene, and 1,2,4-trichlorobenzene. Examples of the ether solvent include tetrahydrofuran, methyltetrahydrofuran, diethyl ether, dipropyl ether, diisopropyl ether, dibutyl ether, dipentyl ether, dihexyl ether, diheptyl ether, dioctyl ether, t-butyl methyl ether, cyclopentyl methyl ether, 1,2-dimethoxyethane, diethylene glycol dimethyl ether, anisol, and diphenyl ether. Examples of the alcohol solvent include methanol, ethanol, 11-propanol, 2-propanol, 1-butanol, isobutyl alcohol, t-butyl alcohol, 1-pentanol, 2-pentanol, isopentyl alcohol, 1-hexanol, 2-hexanol, isohexyl alcohol, 1-heptanol, 2-heptanol, 3-heptanol, isoheptyl alcohol, ethylene glycol monomethyl ether, ethylene glycol monoethyl ether, ethylene glycol monopropyl ether, ethylene glycol monoisopropyl ether, ethylene glycol monobutyl ether, ethylene glycol monoisobutyl ether, ethylene glycol mono-t-butyl ether, diethylene glycol monomethyl ether, diethylene glycol monoethyl ether, diethylene glycol monopropyl ether, diethylene glycol monoisopropyl ether, diethylene glycol monobutyl ether, diethylene glycol monoisobutyl ether, and diethylene glycol mono-t-butyl ether. Examples of the nitrile solvent include acetonitrile, propionitrile, and benzonitrile. Examples of the ester solvent include ethyl acetate, propyl acetate, isopropyl acetate, butyl acetate, isobutyl acetate, t-butyl acetate, amyl acetate, and isoamyl acetate. Examples of the chlorinated aliphatic hydrocarbon solvent include dichloromethane, chloroform, and 1,2-dichloroethane. Examples of the aprotic polar solvent include dimethyl sulfoxide, sulfolane, N,N-dimethylformamide, N,N-dimethylacetamide, N,N-dimethylpropionamide, N-methylpyrrolidone, γ-butyrolactone, dimethyl carbonate, diethyl carbonate, ethylene carbonate, propylene carbonate, 1,3-dimethyl-2-imidazolidinone, and 1,3-dimethyl-3,4,5,6-tetrahydro-2(1H)-pyridinone.

The solvent used in the present catalytic reaction is preferably used as a mixture of water and the solvent other than water, more preferably a mixture of water and an aromatic solvent or an ether solvent, and further preferably a mixture of water and toluene or t-butyl methyl ether.

The amount of the compound (2) used in the present catalytic reaction is preferably within a range from 0.8 to 20 mol, and more preferably within a range from 0.9 to 5 mol, based on 1 mol of the compound (1).

The amount of the compound (5) used in the present catalytic reaction is not limited, and is preferably within a range from 0.00001 to 0.2 mol, and more preferably within a range from 0.0005 to 0.01 mol, based on 1 mol of the compound (1).

The amount of the base used in the present catalytic reaction is preferably within a range from 2 to 30 mol, and more preferably within a range from 4 to 15 mol, based on 1 mol of the compound (1).

When the present catalytic reaction is performed in the presence of a solvent, the amount of the solvent is not limited, and is preferably within a range from 1 to 100 mL, and more preferably within a range from 3 to 30 mL, based on 1 g of the compound (1).

The reaction temperature of the present catalytic reaction is not selected preferably from a range from −30 to 70° C. and more preferably from a range from −10 to 40° C.

The reaction time of the present catalytic reaction can be adjusted according to the amount of the compound (5), the reaction temperature and the like, and the reaction time is preferably within a range from 1 to 120 hours.

The degree of the progress of the present catalytic reaction can be confirmed, for example, by analysis means such as gas chromatography or liquid chromatography.

The mixing method of reaction reagents in the present catalytic reaction is not limited, and examples include a method of mixing compound (1) with a solvent as necessary, adding compound (2) and compound (5) thereto, then adjusting the temperature of the obtained mixture to the reaction temperature, and adding a base to the mixture adjusted to the reaction temperature.

When the optically active compound (5) is used, the compound (3) obtained after completion of the present catalytic reaction is optically active, and the optical purity thereof is, for example, within a range from about 60% e.e. to about 95% e.e.

When the optically active compound (3) is obtained as a mixture with a diastereomer (3c-d), from the viewpoint of facilitating the purification of the compound (3), it is preferable to convert the diastereomer (3c-d) into a 7-membered ring compound represented by formula (8) (compound (8))

(8)

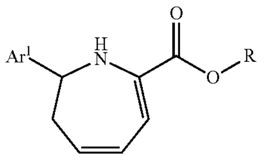

(wherein $Ar^1$ and R are as defined above). The diastereomer (3c-d) can be converted into the 7-membered ring compound (7) under the above-mentioned conditions of the present reaction (see Non-patent Document 1). However, when the diastereomer (3c-d) is not converted into the compound (8) or is insufficiently converted into the compound (8), the diastereomer (3c-d) can be converted into the compound (8) by, for example, heating to about 50° C. to about 80° C. The heating time is preferably from about 1 minute to about 10 hours.

After the conversion of the diastereomer (3c-d) into the compound (8), a ratio of the compound (3) to the compound (8), for example, compound (3):compound (8) is within a range from about 8:1 to about 40:1.

The obtained compound (3) may be isolated and may not be isolated. When the compound is isolated, the reaction mixture obtained after completion of the present catalytic reaction may be subjected to a post-treatment such as neutralization, extraction washing, washing with water or concentration, and may be subjected to an adsorption treatment such as an activated carbon treatment, a silica treatment or an alumina treatment, and a purification treatment such as recrystallization, distillation or silica gel column chromatography, as necessary.

Compound (4) represented by formula (4) (compound (4))

(4)

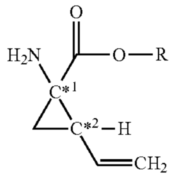

(wherein R, $C^{*1}$ and $C^{*2}$ are as defined above) is obtained by imine-hydrolysis of the thus obtained compound (3). The imine-hydrolysis herein means that an arylmethylideneamino group contained in the compound (3) is converted into an amino group.

There is no limitation on the imine-hydrolysis, as long as the method does not cause hydrolysis of an ester moiety contained in the compound (3), and the imine-hydrolysis is preferably carried out by mixing the compound (3) with an acid.

Examples of the acid used for the imine-hydrolysis include inorganic acids such as hydrochloric acid, sulfuric acid, phosphoric acid, nitric acid, and perchloric acid.

The acid may be used singly or in a mixture with the below-mentioned solvent.

The acid is preferably an inorganic acid, and more preferably hydrochloric acid. When hydrochloric acid is used as the acid, the concentration may be appropriately adjusted by mixing with water or the like.

In the imine-hydrolysis, the amount of the acid is preferably adjusted so that the mixture obtained after mixing with the acid has a pH within a range from 0 to 4. In order to adjust the pH within the above range, when the acid is hydrochloric acid, for example, the acid may be used in an amount of 0.8 to 1.5 mol, based on 1 mol of the compound (3).

The imine-hydrolysis is preferably carried out in a solvent. Examples of the solvent used in the imine-hydrolysis include the same solvents as those described above used in the present catalytic reaction.

The solvent may be alone or a mixture of two or more kinds thereof.

The solvent is preferably water, an aromatic solvent, or an ether solvent.

The amount of the solvent is in a range from 1 to 100 mL, and preferably in a range from 3 to 30 mL, based on 1 g of the compound (3).

The temperature, at which the imine-hydrolysis is carried out, is, for example, selected from a range of 0 to 80° C., preferably 5 to 60° C., and more preferably 10 to 40° C.

The time to carry out the imine-hydrolysis can be adjusted according to the kind and concentration of the acid to be used, and the temperature at which the imine-hydrolysis is carried out, and is preferably within a range from 1 minute to 20 hours, and more preferably within a range from 10 minutes to 10 hours.

There is no limitation on the mixing method in the imine-hydrolysis, and examples include a method in which compound (3) is mixed with a solvent and an acid is added to the obtained mixture.

When the optically active compound (3) is subjected to the imine hydrolysis, the optical purity of the compound (4) obtained after completion of the imine-hydrolysis is nearly equivalent to the optical purity of the compound (3) subjected to the imine hydrolysis, for example, within a range from about 60% e.e. to about 95% e.e.

When the obtained compound (4) is isolated, the reaction mixture obtained from the imine-hydrolysis may be subjected to a post-treatment such as neutralization, extraction washing, washing with water or concentration, and may be subjected to an adsorption treatment such as an activated carbon treatment, a silica treatment or an alumina treatment, and a purification treatment such as distillation or silica gel column chromatography, as necessary.

Examples of the compound (4) include (1S,2R)-1-amino-2-vinylcyclopropanecarboxylic acid ethyl ester, (1S,2R)-1-amino-2-vinylcyclopropanecarboxylic acid t-butyl ester, (1S,2R)-1-amino-2-vinylcyclopropanecarboxylic acid methyl ester, (1R,2S)-1-amino-2-vinylcyclopropanecarboxylic acid ethyl ester, (1R,2S)-1-amino-2-vinylcyclopropanecarboxylic acid t-butyl ester, and (1R,2S)-1-amino-2-vinylcyclopropanecarboxylic acid methyl ester.

EXAMPLES

Hereinafter, the present invention will be described in more detail below by way of Examples.

Production of Compound (7-2)

(S)-2-amino-1,1-di-p-tolyl-1-propanol p-Tolylmagnesium bromide (1.0 mol/L-tetrahydrofuran solution) (35 mL (35.0 mmol)) was cooled to 5° C., and a mixed solution of 7.66 g of a toluene solution of (S)-alanine benzyl ester (pure (S)-alanine benzyl ester 1.79 g, 10.0 mmol) and 35 mL of toluene was added dropwise thereto over 1.5 hours. After completion of the dropwise addition, the obtained mixture was stirred at 5° C. for 30 minutes, further heated to room temperature and stirred for 2 hours. After completion of the reaction, the reaction mixture was ice-cooled, and 17.5 mL of an aqueous 2 mol/L hydrochloric acid (HCl 35.0 mmol) was added dropwise thereto. Thereafter, stirring was stopped to perform liquid separation, and the obtained organic layer was washed twice with 20 mL of 20% brine. The washed organic layer was dried over magnesium sulfate and then purified by silica gel column chromatography to obtain 1.61 g (6.32 mmol) of (S)-2-amino-1,1-di-p-tolyl-1-propanol. Yield: 63%.

Production of Compound (7-3)

(S)-2-(benzylamino)-1,1-di-p-tolyl-1-propanol (S)-2-amino-1,1-di-p-tolyl-1-propanol obtained above (1.60 g (6.25 mmol)) and 10 mL of toluene were mixed, and 0.66 g (6.25 mmol) of benzaldehyde and 1.60 g of magnesium sulfate were added to the mixture at room temperature, then the mixture was stirred for 2 hours. The obtained mixture was filtered to remove magnesium sulfate, and the filtrate was concentrated to obtain an imine compound.

The obtained imine compound (0.87 g (2.5 mmol)) was separated, and the separated imine compound and 10 mL of acetonitrile were mixed, then 0.19 g (5.0 mmol) of sodium borohydride was added to the mixture at room temperature. Sodium bicarbonate water (5% by weight) was added dropwise to the mixture, and 10 mL of toluene and 10 mL of ethyl acetate were flown thereinto. An aqueous 1 mol/L hydrochloric acid was added to the obtained mixture, and the pH of the aqueous layer was adjusted to 8 to 9, then stirring was stopped to perform liquid separation, and the obtained organic layer was washed with 5 mL of 20% by weight brine. The aqueous layers each obtained were combined, and the mixture was extracted with 10 mL of ethyl acetate. The previously obtained organic layer and the organic layer obtained by extraction with ethyl acetate were combined, and the mixture was dried over sodium sulfate, then purified by silica gel column chromatography to obtain 0.84 g (2.44 mmol) of (S)-2-(benzylamino)-1,1-di-p-tolyl-1-propanol. Yield: 97%.

Production of Compound (7-4)

(S)—N-benzyl-N-methyl-1-methoxy-1,1-di-p-tolyl-2-propylamine (S)-2-(benzylamino)-1,1-di-p-tolyl-1-propanol obtained above (0.84 g (2.4 mmol)) and 10 mL of tetrahydrofuran were mixed and ice-cooled. Thereto were added 1.04 g (7.32 mmol) of iodomethane and 0.22 g (content 60%, 6.1 mmol) of sodium hydride. The obtained mixture was heated to room temperature and stirred for 2 hours, then 5 mL of dimethylformamide was flown thereinto and stirred for further 13 hours. Toluene (10 mL) was flown into the obtained mixture, and after ice cooling, 10 mL of water was added dropwise. Stirring was stopped to perform liquid separation, and the aqueous layer was extracted with 10 mL of toluene. The organic layers each obtained were combined, thereafter the mixture was washed with 5 mL of 20% by weight brine and dried over sodium sulfate, then purified by silica gel column chromatography to obtain (S)—N-benzyl-N-methyl-1-methoxy-1,1-di-p-tolyl-2-propylamine. Yield: 81%.

Production of Compound (7)

(S)—N-methyl-1-methoxy-1,1-di-p-tolyl-2-propylamine (S)—N-benzyl-N-methyl-1-methoxy-1,1-di-p-tolyl-2-propylamine obtained above (0.83 g (2.2 mmol)) and 10 mL of ethanol were flown into an autoclave vessel, and 0.80 g of 10% palladium-carbon (manufactured by Kawaken Fine Chemicals Co., Ltd., NX type, 50% wet) was added to the solution at room temperature. The inside of this autoclave vessel was replaced with nitrogen at a nitrogen pressure of 0.2 MPa three times, then replaced with hydrogen at a hydrogen pressure of 0.4 MPa three times, and the obtained mixture was stirred at 40° C. for 2 hours under the condition of a hydrogen pressure of 0.5 MPa. After the reaction, the inside of the vessel was replaced with nitrogen at a nitrogen pressure of 0.2 MPa three times, then the pressure was returned to normal pressure, and the obtained reaction mixture was filtered to remove palladium-carbon. The obtained filtrate was concentrated to obtain 0.62 g of (S)—N-methyl-1-methoxy-1,1-ditolyl-2-propylamine. Yield: 100%

Example 1

Production of Compound (5)

(S)-2,10-di-t-butyl-3,9-dimethoxy-6-methyl-6-(1-methyl-2-methoxy-2,2-di-p-tolylethyl)-4,8-bis(3,5-bistrifluoromethylphenyl)-6,7-dihydro-5H-dibenzo[c,e]-azepinium bromide (S)—N-methyl-1-methoxy-1,1-di-p-tolyl-2-propylamine obtained above (0.62 g (2.2 mmol)) and 10 mL of acetone were mixed, and 1.73 g (1.85 mmol) of 5,5'-di-t-butyl-4,4'-dimethoxy-2,2'-bisdibromomethyl-3,3'-(3,5-bistrifluoromethylphenyl)-biphenyl and 0.17 g (2.01 mmol) of sodium bicarbonate were added to the obtained mixture. The obtained mixture was heated in an oil bath at 57° C., and reacted for 28 hours. After completion of the reaction, the temperature of the oil bath was cooled to 50° C., then 10 mL of cyclohexane was flown thereinto, and the mixture was washed twice with 5 mL of water. The obtained organic layer was concentrated, then cyclohexane was added to the residue, and the obtained mixture was stirred while heating in an oil bath at 50° C. to obtain a slurry. This slurry was cooled to room temperature, and crystal powder was taken out by filtration and dried under reduced pressure to obtain 1.34 g (1.18 mmol) of (S)-2,10-di-t-butyl-3,9-dimethoxy-6-methyl-6-(1-methyl-2-methoxy-2,2-di-p-tolylethyl)-4,8-bis(3,5-bistrifluoromethylphenyl)-6,7-dihydro-5H-dibenzo[c,e]-azepinium bromide. Yield: 64%.

$^{1}$H-NMR ($CDCl_3$, 400 MHz) δ ppm: 8.20 (1H, s), 8.15 (1H, s), 8.10 (1H, s), 8.06 (1H, s), 7.90 (1H, s), 7.74 (1H, s), 7.61 (1H, s), 7.54 (1H, s), 7.14 (2H, d, J=7.8 Hz), 6.91 (2H, d, J=7.8 Hz), 6.85 (2H, d, J=8.3 Hz), 6.73 (2H, d, J=8.3 Hz), 5.30 (1H, d, J=15.1 Hz), 4.62-4.50 (1H, m), 4.20 (1H, d, J=12.7 Hz), 4.02-3.90 (2H, m), 3.12 (3H, s), 3.01 (3H, s), 2.58 (3H, s), 2.35 (3H, s), 2.29 (3H, s), 2.23 (3H, s), 1.57 (9H, s), 1.49 (9H, s), 0.58 (3H, d, J=6.8 Hz).

Examples 2 to 6

Tolylmagnesium bromide in the production of (S)-2-amino-1,1-di-p-tolyl-1-propanol was changed to an organic magnesium halide shown in the following Table 1 to produce compound (5) shown in the following Table 1.

TABLE 1

| | Organic magnesium halide | Compound (5) |
|---|---|---|
| Example 2 | Ethylmagnesium bromide | 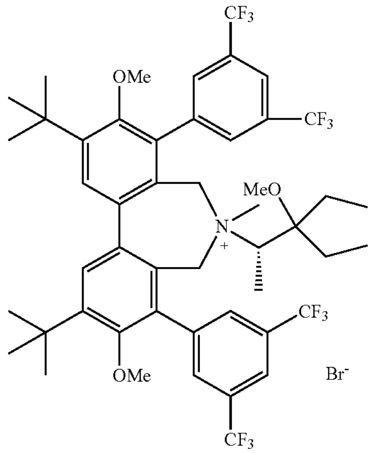 |
| Example 3 | n-Butylmagnesium chloride | 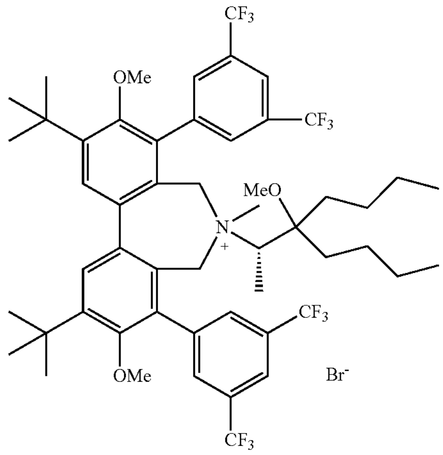 |

TABLE 1-continued
| | Organic magnesium halide | Compound (5) |
|---|---|---|
| Example 4 | n-Hexylmagnesium chloride | 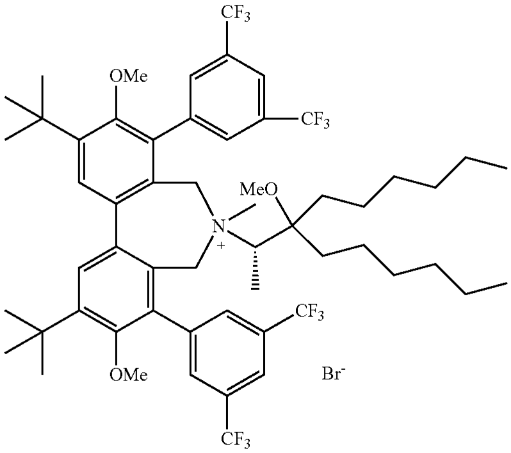 |
| Example 5 | n-Octylmagnesium bromide | 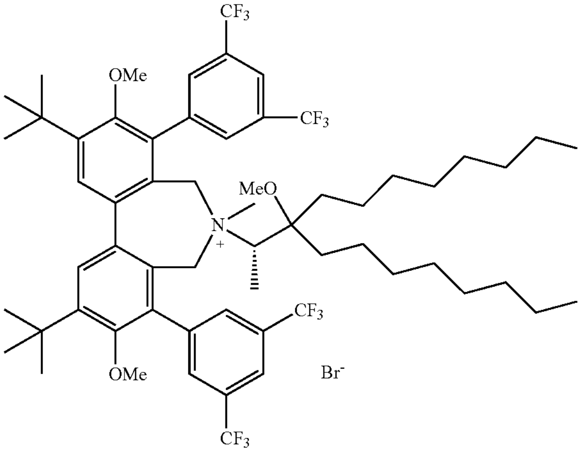 |
| Example 6 | Phenylethynylmagnesium chloride | 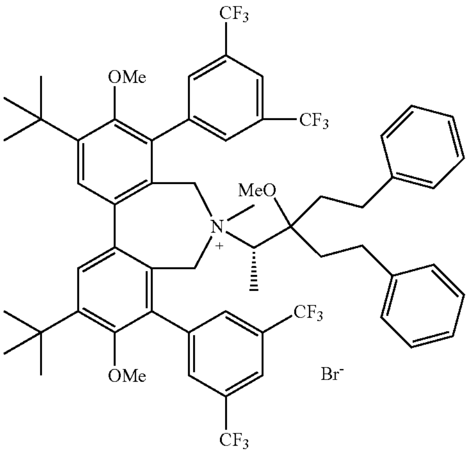 |

Compound (5) Obtained in Example 2

(S)-2,10-di-t-butyl-3,9-dimethoxy-6-methyl-6-(1-methyl-2-methoxy-2-ethylbutyl)-4,8-bis(3,5-bistrifluoromethylphenyl)-6,7-dihydro-5H-dibenzo[c,e]-azepinium bromide $^1$H-NMR ($CDCl_3$, 400 MHz) 8 ppm: 8.35 (1H, s), 8.19 (1H, s), 8.01 (1H, s), 8.00 (1H, s), 7.84 (1H, s), 7.71 (1H, s), 7.63 (1H, s), 7.57 (1H, s), 5.41 (1H, d, J=15.1 Hz), 4.42 (1H, d, J=13.7 Hz), 3.90 (1H, d, J=15.1 Hz), 3.82 (1H, d, J=13.7 Hz), 3.24 (3H, s), 3.03 (3H, s), 3.02-2.95 (1H, m), 2.90 (3H, s), 2.83 (3H, s), 1.80-1.20 (3H, m), 1.57 (9H, s), 1.49 (9H, s), 1.02-0.90 (1H, m), 0.77-0.68 (5H, m), 0.57 (3H, t, J=7.3 Hz).

Compound (5) Obtained in Example 3

(S)-2,10-di-t-butyl-3,9-dimethoxy-6-methyl-6-(1-methyl-2-methoxy-2-butylhexyl)-4,8-bis(3,5-bistrifluoromethylphenyl)-6,7-dihydro-5H-dibenzo[c,e]-azepinium bromide $^1$H-NMR ($CDCl_3$, 400 MHz) δ ppm: 8.34 (1H, s), 8.18 (1H, s), 8.01 (1H, s), 7.99 (1H, s), 7.82 (1H, s), 7.70 (1H, s), 7.62 (1H, s), 7.57 (1H, s), 5.45 (1H, d, J=15.1 Hz), 4.52 (1H, d, J=13.2 Hz), 3.89 (1H, d, J=15.1 Hz), 3.77 (1H, d, J=13.2 Hz), 3.19 (3H, s), 3.04 (3H, s), 3.09-2.99 (1H, m), 2.87 (3H, s), 2.76 (3H, s), 1.60-0.77 (12H, m), 1.53 (9H, s), 1.50 (9H, s), 0.83 (3H, t, J=7.3 Hz), 0.78-0.66 (5H, m).

Compound (5) Obtained in Example 4

(S)-2,10-di-t-butyl-3,9-dimethoxy-6-methyl-6-(1-methyl-2-methoxy-2-hexyloctyl)-4,8-bis(3,5-bistrifluoromethylphenyl)-6,7-dihydro-5H-dibenzo[c,e]-azepinium bromide $^1$H-NMR ($CDCl_3$, 400 MHz) 8 ppm: 8.36 (1H, s), 8.17 (1H, s), 8.02 (1H, s), 7.98 (1H, s), 7.81 (1H, s), 7.70 (1H, s), 7.62 (1H, s), 7.57 (1H, s), 5.50 (1H, d, J=15.1 Hz), 4.53 (1H, d, J=13.2 Hz), 3.87 (1H, d, J=15.1 Hz), 3.75 (1H, d, J=13.2 Hz), 3.19 (3H, s), 3.05 (3H, s), 3.08-2.98 (1H, m), 2.85 (3H, s), 2.74 (3H, s), 1.52 (9H, s), 1.49 (9H, s), 1.40-0.66 (20H, m), 0.87 (3H, t, J=7.3 Hz), 0.86 (3H, t, J=7.3 Hz), 0.72 (3H, d, J=6.8 Hz).

Compound (5) Obtained in Example 5

(S)-2,10-di-t-butyl-3,9-dimethoxy-6-methyl-6-(1-methyl-2-methoxy-2-octyldecanyl)-4,8-bis(3,5-bistrifluoromethylphenyl)-6,7-dihydro-5H-dibenzo[c,e]-azepinium bromide $^1$H-NMR ($CDCl_3$, 400 MHz) δ ppm: 8.36 (1H, s), 8.16 (1H, s), 8.01 (1H, s), 7.97 (1H, s), 7.80 (1H, s), 7.70 (1H, s), 7.62 (1H, s), 7.57 (1H, s), 5.51 (1H, d, J=15.1 Hz), 4.53 (1H, d, J=13.2 Hz), 3.86 (1H, d, J=15.1 Hz), 3.74 (1H, d, J=13.2 Hz), 3.19 (3H, s), 3.05 (3H, s), 3.08-3.00 (1H, m), 2.85 (3H, s), 2.74 (3H, s), 1.52 (9H, s), 1.49 (9H, s), 1.40-0.65 (28H, m), 0.90 (3H, t, J=6.8 Hz), 0.88 (3H, t, J=6.8 Hz), 0.72 (3H, d, J=6.8 Hz).

Compound (5) Obtained in Example 6

(S)-2,10-di-t-butyl-3,9-dimethoxy-6-methyl-6-[4-phenyl-1-methyl-2-methoxy-2-(2-phenylethyl)butyl]-4,8-bis(3,5-bistrifluoromethylphenyl)-6,7-dihydro-5H-dibenzo[c,e]-azepinium bromide $^1$H-NMR ($CDCl_3$, 400 MHz) δ ppm: 8.39 (1H, s), 8.11 (1H, s), 7.99 (1H, s), 7.84 (1H, s), 7.62 (1H, s), 7.60 (1H, s), 7.59 (1H, s), 7.49 (1H, s), 7.40-7.22 (6H, m), 7.06-7.00 (2H, m), 6.83-6.75 (2H, m), 5.64 (1H, d, J=15.1 Hz), 4.59 (1H, d, J=13.7 Hz), 3.96-83 (2H, m), 3.25-3.12 (1H, m), 3.11 (3H, s), 3.03 (3H, s), 2.97 (3H, s), 2.92 (3H, s), 2.58-2.24 (4H, m), 1.80-1.10 (4H, m), 1.52 (9H, s), 1.50 (9H, s), 0.90 (3H, d, J=6.8 Hz).

Production of Compound (1): (E)-N-phenylmethyleneglycine ethyl ester

Glycine ethyl ester hydrochloride (13.8 g (98.9 mmol)) and 50 g of toluene were mixed, and 10 g of dimethyl sulfoxide was flown thereinto at room temperature. Benzaldehyde (10.0 g (94.2 mmol)) was flown into the obtained mixture. The obtained mixture was adjusted to 12° C., and 16.5 g of a 25% aqueous sodium hydroxide solution (sodium hydroxide 104 mmol) was added dropwise over 3 hours. After completion of the dropwise addition, the obtained mixture was stirred at a temperature in a range from 11° C. to 13° C. for 20 hours. After completion of the reaction, the reaction mixture was cooled to 5° C., and 11.4 mL of water was added dropwise thereto. Thereafter, stirring was stopped to perform liquid separation, and the obtained organic layer was washed with 19 g of 20% by weight brine. The obtained organic layer was dried over magnesium sulfate, then the solvent was distilled off under reduced pressure to obtain 43.6 g of a toluene solution of (E)-N-phenylmethyleneglycine ethyl ester (16.5 g of pure (E)-N-phenylmethyleneglycine ethyl ester). Yield: 92%

Example 7

Production of Compound (3)

(1R,2S)-1-(N-phenylmethylene)amino-2-vinylcyclopropanecarboxylic acid ethyl ester A toluene solution (2.60 g) of (E)-N-phenylmethyleneglycine ethyl ester (pure (E)-N-phenylmethyleneglycine ethyl ester: 0.98 g, 5.14 mmol) and 10 mL of toluene were mixed, and 1.00 g (4.68 mmol) of (E)-1,4-dibromo-2-butene and 0.027 g (0.023 mmol) of (S)-2,10-di-t-butyl-3,9-dimethoxy-6-methyl-6-(1-methyl-2-methoxy-2,2-di-p-tolylethyl)-4,8-bis(3,5-bistrifluoromethylphenyl)-6,7-dihydro-5H-dibenzo[c,e]-azepinium bromide obtained in Example 1 were added thereto at room temperature. The obtained mixture was cooled to 0° C., then 5.25 g of a 50% aqueous potassium hydroxide solution (46.8 mmol of potassium hydroxide) was added thereto, and the mixture was stirred at 0° C. to react (E)-N-phenylmethyleneglycine ethyl ester with (E)-1,4-dibromo-2-butene. The reaction time was 20 hours. After completion of the reaction, 3 mL of water was added to the obtained mixture, then stirring was stopped to perform liquid separation, and the obtained organic layer was washed with 3 mL of 20% brine. After liquid separation, the organic layer containing the titled (1R,2S)-1-(N-phenylmethylene)amino-2-vinylcyclopropanecarboxylic acid ethyl ester was obtained.

(1R,2S)-1-(N-phenylmethylene)amino-2-vinylcyclopropanecarboxylic acid ethyl ester contained in the organic layer was analyzed under the following analytical conditions of high-performance liquid chromatography, and the ratio of (1R,2S)-1-(N-phenylmethylene)amino-2-vinylcyclopropanecarboxylic acid ethyl ester to ethyl 7-phenyl-6,7-dihydro-1H-azepine-2-carboxylate as compound (8) was calculated. (1R,2S)-1-(N-phenylmethylene)amino-2-vinylcyclopropanecarboxylic acid ethyl ester:ethyl 7-phenyl-6,7-dihydro-1H-azepine-2-carboxylate=10:1

A diastereomer of (1R,2S)-1-(N-phenylmethylene)amino-2-vinylcyclopropanecarboxylic acid ethyl ester was not detected.

<Analytical Conditions of High-Performance Liquid Chromatography>

Column: YMC Pack ODS-A-302 (4.6×150 mm, 5 μm)

Mobile phase: A=aqueous 40 mM $KH_2PO_4$ (pH 3.5—$H_3PO_4$),

B=methanol

A/B=10% (0 min)→10% (5 min)→70% (25 min)→70% (45 min)

Flow rate: 1.0 mL/minute

Detector: wavelength of 220 nm

Retention time:

11.7 minutes ((1R,2S)-1-(N-phenylmethylene)amino-2-vinylcyclopropanecarboxylic acid ethyl ester)

31.2 minutes (ethyl 7-phenyl-6,7-dihydro-1H-azepine-2-carboxylate)

<Determination of Yield and Optical Purity>

Subsequently, 4.7 mL of an aqueous 1 M hydrochloric acid was added to the obtained organic layer, and a hydrolysis reaction was carried out by stirring at room temperature for 2 hours. After completion of the reaction, liquid separation was carried out, and the obtained organic layer was extracted by adding 3 mL of water. The obtained aqueous layers were combined to obtain 7.93 g of an aqueous solution of (1R,2S)-1-amino-2-vinylcyclopropanecarboxylic acid ethyl ester hydrochloride. The obtained aqueous solution was subjected to quantitative analysis under the above analytical conditions, and the yield was calculated. Yield: 59%. In addition, the optical purity was determined by analyzing the obtained aqueous solution under the following conditions for optical purity analysis. Optical purity: 81% e.e.

<Conditions for Optical Purity Analysis>

Column: CHIRALPAK (registered trademark of Daicel Chemical Industries, Ltd.) AD-RH (4.6×150 mm, 5 μm)

Mobile phase:

A=20 mM aqueous dipotassium hydrogenphosphate solution (adjusted to pH of 8.0 with phosphoric acid), B=acetonitrile

A/B=80/20

Flow rate: 0.5 mL/minute

Detector: wavelength of 215 nm

Retention time: (1R,2S) isomer=14.7 minutes, (1S,2R) isomer=16.2 minutes

Examples 8 to 12

According to the method of Example 7 except for using the compound (5) obtained in Examples 2 to 6, in place of (S)-2,10-di-t-butyl-3,9-dimethoxy-6-methyl-6-(1-methyl-2-methoxy-2,2-di-p-tolylethyl)-4,8-bis(3,5-bistrifluoromethylphenyl)-6,7-dihydro-5H-dibenzo[c,e]-azepinium bromide, (1R,2S)-1-(N-phenylmethylene)amino-2-vinylcyclopropanecarboxylic acid ethyl ester was obtained. The use amount of the compound (5) was 0.005 mol based on 1 mol of (E)-1,4-dibromo-2-butene. The result is shown in Table 2.

TABLE 2

| | Compound (5) | Yield | Optical purity | Compound (3) Compound (8) |
|---|---|---|---|---|
| Example 8 | 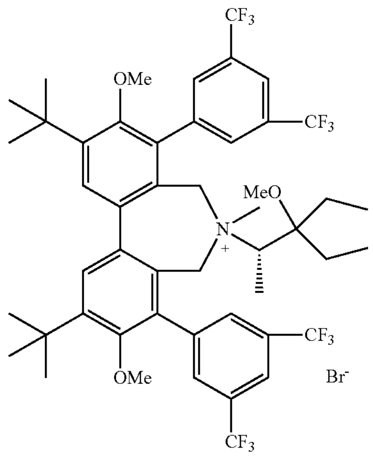 | 65% | 73% ee | 18:1 |

TABLE 2-continued
| | Compound (5) | Yield | Optical purity | Compound (3) Compound (8) |
|---|---|---|---|---|
| Example 9 | 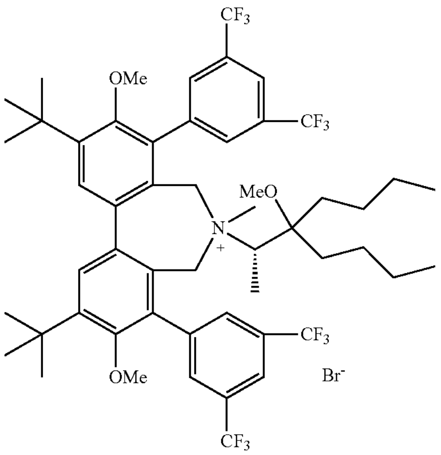 | 68% | 80% ee | 22:1 |
| Example 10 | 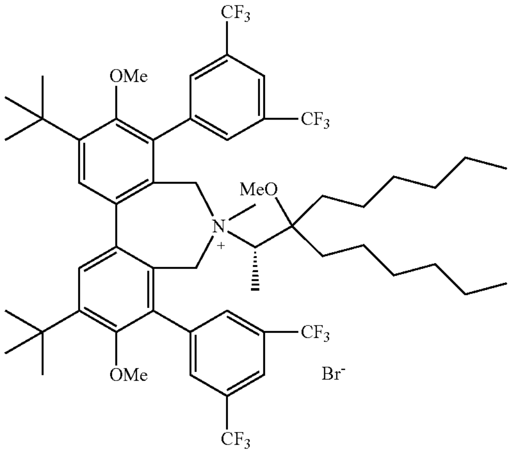 | 66% | 79% ee | 21:1 |
| Example 11 | 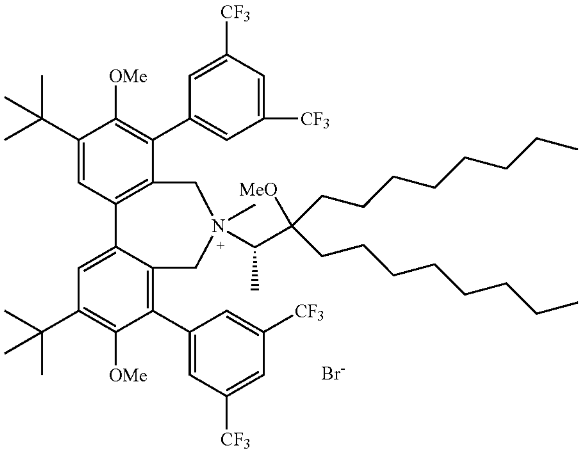 | 66% | 79% ee | 21:1 |

TABLE 2-continued

| | Compound (5) | Yield | Optical purity | Compound (3) Compound (8) |
|---|---|---|---|---|
| Example 12 | 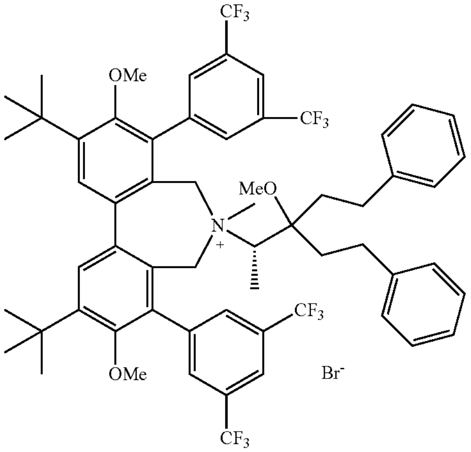 | 67% | 84% ee | 30:1 |

INDUSTRIAL APPLICABILITY

The compound (5) of the present invention is useful in the production of compound (3). The compound (3) such as (1R, 2S)-1-(N-phenylmethylene)amino-2-vinylcyclopropanecarboxylic acid ester is useful as a production intermediate of pharmaceuticals such as anti-hepatitis C agent.

The invention claimed is:

1. A quaternary ammonium salt represented by formula (5)

(5)

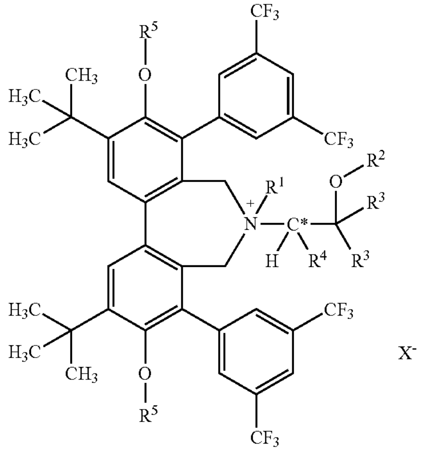

(wherein $R^1$ represents an alkyl group having 1 to 4 carbon atoms, $R^2$ represents an alkyl group having 1 to 10 carbon atoms, $R^3$ represents an alkyl group having 1 to 10 carbon atoms that is optionally substituted with one or more phenyl groups; or a phenyl group that optionally has one or more groups selected from the group consisting of alkyl groups having 1 to 10 carbon atoms and a trifluoromethyl group, $R^4$ represents an alkyl group having 1 to 4 carbon atoms, $R^5$ represents an alkyl group having 1 to 10 carbon atoms, C* represents an asymmetric carbon atom, and $X^-$ represents a halide ion).

2. The quaternary ammonium salt according to claim 1, wherein the quaternary ammonium salt represented by formula (5) is an optically active compound based on the asymmetric carbon atom of C*.

3. The quaternary ammonium salt according to claim 1, wherein both $R^1$ and $R^4$ in formula (5) are a methyl group.

4. The quaternary ammonium salt according to claim 1, wherein both $R^2$ and $R^5$ in formula (5) are a methyl group.

5. The quaternary ammonium salt according to claim 1, wherein $R^3$ in formula (5) is an ethyl group, a butyl group, a hexyl group, an octyl group, a 2-phenylethyl group, or a p-tolyl group.

6. A method for producing a cyclopropane compound represented by formula (3)

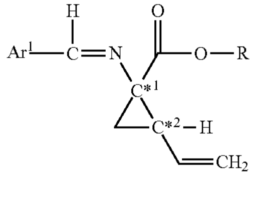

(3)

(wherein $Ar^1$ represents an optionally substituted phenyl group or an optionally substituted naphthyl group, and R represents an alkyl group having 1 to 12 carbon atoms or an alkenyl group having 2 to 12 carbon atoms, $C^{*1}$ and $C^{*2}$ represent an asymmetric carbon atom, $C^{*2}$ is an S-configuration when $C^{*1}$ is an R-configuration, and $C^{*2}$ is an R-configuration when $C^{*1}$ is an S-configuration), comprising a step of reacting a compound represented by formula (1)

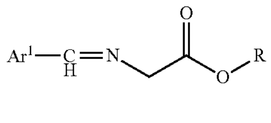

(1)

(wherein $Ar^1$ and R are as defined above)

with a compound represented by formula (2)

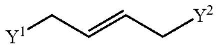

(2)

(wherein $Y^1$ and $Y^2$ each independently represent a halogen atom, an alkanesulfonyloxy group having 1 to 6 carbon atoms, an perfluoroalkanesulfonyloxy group having 1 to 6 carbon atoms, or a benzenesulfonyloxy group, herein, a hydrogen atom or atoms contained in the benzenesulfonyloxy group may be each independently substituted with one or more groups selected from the group consisting of alkyl groups having 1 to 6 carbon atoms, halogen atoms, and a nitro group), in the presence of a quaternary ammonium salt represented by formula (5)

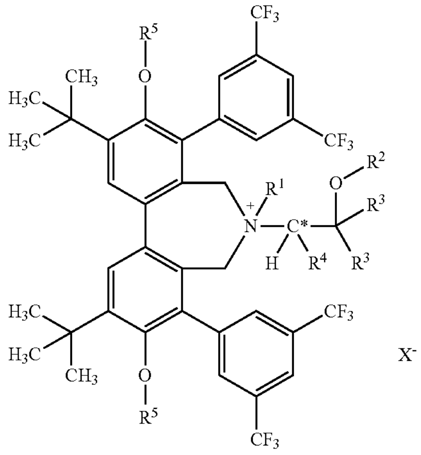

(5)

(wherein $R^1$ represents an alkyl group having 1 to 4 carbon atoms, $R^2$ represents an alkyl group having 1 to 10 carbon atoms, $R^3$ represents an alkyl group having 1 to 10 carbon atoms that is optionally substituted with one or more phenyl groups; or a phenyl group that optionally has one or more groups selected from the group consisting of alkyl groups having 1 to 10 carbon atoms and a trifluoromethyl group, $R^4$ represents an alkyl group having 1 to 4 carbon atoms, $R^5$ represents an alkyl group having 1 to 10 carbon atoms, C* represents an asymmetric carbon atom, and $X^-$ represents a halide ion) and a base.

7. The production method according to the claim 6, wherein the quaternary ammonium salt represented by formula (5) and the cyclopropane compound represented by formula (3) are both optically active.

8. The quaternary ammonium salt according to claim 2, wherein both $R^1$ and $R^4$ in formula (5) are a methyl group.

9. The quaternary ammonium salt according to claim 2, wherein both $R^2$ and $R^5$ in formula (5) are a methyl group.

10. The quaternary ammonium salt according to claim 3, wherein both $R^2$ and $R^5$ in formula (5) are a methyl group.

11. The quaternary ammonium salt according to claim 2, wherein $R^3$ in formula (5) is an ethyl group, a butyl group, a hexyl group, an octyl group, a 2-phenylethyl group, or a p-tolyl group.

12. The quaternary ammonium salt according to claim 3, wherein $R^3$ in formula (5) is an ethyl group, a butyl group, a hexyl group, an octyl group, a 2-phenylethyl group, or a p-tolyl group.

13. The quaternary ammonium salt according to claim 4, wherein $R^3$ in formula (5) is an ethyl group, a butyl group, a hexyl group, an octyl group, a 2-phenylethyl group, or a p-tolyl group.

* * * * *